(12) United States Patent
Cho et al.

(10) Patent No.: US 9,283,245 B2
(45) Date of Patent: Mar. 15, 2016

(54) COMPOSITION CONTAINING PIAS3 AS AN ACTIVE INGREDIENT FOR PREVENTING OR TREATING CANCER OR IMMUNE DISEASE

(75) Inventors: Mi-La Cho, Seoul (KR); Seon-Yeong Lee, Suwon (KR); Young-Mee Moon, Seoul (KR); Jun-Geol Ryu, Taebak (KR); Yang-Mi Her, Ansan (KR); Hye-Jwa Oh, Seoul (KR)

(73) Assignee: CATHOLIC UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 504 days.

(21) Appl. No.: 13/697,789

(22) PCT Filed: Oct. 29, 2010

(86) PCT No.: PCT/KR2010/007504
§ 371 (c)(1),
(2), (4) Date: Nov. 13, 2012

(87) PCT Pub. No.: WO2011/142514
PCT Pub. Date: Nov. 17, 2011

(65) Prior Publication Data
US 2013/0189240 A1    Jul. 25, 2013

(30) Foreign Application Priority Data

May 13, 2010  (KR) .................. 10-2010-0045058

(51) Int. Cl.
*A61K 48/00*     (2006.01)
*A61K 31/7105*   (2006.01)
*C07K 14/47*     (2006.01)

(52) U.S. Cl.
CPC ........... *A61K 31/7105* (2013.01); *A61K 48/005* (2013.01); *C07K 14/4703* (2013.01)

(58) Field of Classification Search
None
See application file for complete search history.

(56) References Cited

U.S. PATENT DOCUMENTS

| 7,265,202 B1 | 9/2007 | Shuai et al. |
| 2005/0158808 A1 | 7/2005 | Kikuchi et al. |
| 2006/0269519 A1 | 11/2006 | Chen et al. |

OTHER PUBLICATIONS

MS the disease, 2015, pp. 1-4 Wang et al., 2001, J. Biol. Chem. vol. 276: 49213-49220.*
Whisstock et al., 2003, Quart. Rev. Biophys. vol. 36: 307-340 Quinn et al., 2001, Best. Pract. Res. Clin. Rheum. vol. 15: 49-66.*
Mor et al., 2005, J. Immunol. vol. 175: 3439-3445 Chevalier et al., 2013, Blood. vol. 121: 29-37.*
Progress in Autoimmune Dis. Res.2005, pp. 1-126.*
Yoshitaka Ogata et al., "Overexpression of PIAS3 Suppresses Cell Growth and Restores the Drug Sensitivity of Human Lung Cancer Cells in Association with PI3-K/Akt Inactivation", Neoplasia, Oct. 2006, pp. 817-825, vol. 8, No. 10.
International Search Report for PCT/KR2010/007504 filed on Oct. 29, 2010.

* cited by examiner

*Primary Examiner* — Amy Juedes
(74) *Attorney, Agent, or Firm* — Joseph Hyosuk Kim; JHK Law

(57) ABSTRACT

The present invention relates to a composition containing PIAS3 as an active ingredient for the prevention or treatment of cancer or immune disease. More specifically, the present invention relates to a composition containing the PIAS3 gene or an expressing protein thereof as an active ingredient for the prevention or treatment of cancer or immune disease, to an immunosuppressant composition, to a method for reducing or inhibiting undifferentiated T cells into Th17 cells using the PIAS3 gene or an expressing protein thereof, and to a method for activating regulatory T cells.

4 Claims, 10 Drawing Sheets

COMPOSITION CONTAINING PIAS3 AS AN ACTIVE INGREDIENT FOR PREVENTING OR TREATING CANCER OR IMMUNE DISEASE

CROSS-REFERENCES TO RELATED APPLICATION

This patent application is a U.S. national phase under 35 U.S.C 371 of PCT/KR2010/007504 filed on Oct. 29, 2010, which claims the benefit of priority from Korean Patent Application No. 10-2010-0045058, filed on May 13, 2010, in the Korean Intellectual Property Office, the disclosure of which is incorporated herein by reference in its entirety.

BACKGROUND OF THE INVENTION

1. Field of the Invention

The present invention relates to a pharmaceutical use of protein inhibitor of activated signal transducer and activator of transcription (PIAS3) for prevention or treatment of cancer or immune disease caused due to abnormality in immune response, and more particularly, to a composition containing PIAS3 as an active ingredient for preventing or treating cancer or immune disease.

2. Description of the Related Art

T cells play a central role in immune system as a biological defense system against various pathogens. T cells originate from the thymus and develop into T cells with unique properties through a series of differentiation. After completing differentiation, 1 cells are largely classed into, by function, Type 1 helper cells (Th1) and Type 2 helper cells (Th2). Th1 cells mainly involve in the cell mediated immunity, and Th2 cells involve in humoral immunity. In immune system, these two cell groups maintain a balance through mutual control so that both are not excessively activated.

Accordingly, most of immune diseases is caused due to imbalance between the above two immune cells. For example, abnormal increase of Th1 activity can lead to autoimmune disease, and abnormal increase of Th2 cell activity can lead to immune disease due to hypersensitive reaction.

Meanwhile, recent study on Th1 cell differentiation has reported the presence of regulatory T cells (Treg), the new group that can regulate TM cell activity, and following this, many studies have introduced immunological treatment using the regulatory T cells. Because Treg cells are characterized of inhibiting functions of abnormally activated immune cells to thus control inflammatory reaction, many studies report about experiments designed to treat immune diseases by the mechanism of increasing Treg cell, activity.

Beside Treg cells, Th17 cells are another group that is made in the differentiation process. Th17 cells are known to be developed from non-differentiated T cells in a similar process as Treg cells. That is, differentiation of both Treg cells and Th17 cells is commonly occurs in the presence of TGF-β. However, while Treg cells do not require IL-6, Th17 cells differentiate in the presence of both TGF-β and IL-6. Further, differentiated Th17 cells secret IL-17.

Evidences show that unlike Treg cells, Th17 cells involve in the forefront of inflammation response in an immune disease, maximizing inflammatory response signaling and accelerating progress of the disease. Taking autoimmune disease that is not controlled by Treg cells for example, development of treatment for such autoimmune disease particularly targets inhibition of Th17 cell activity.

The most widely used immune disease treatment for now will be by way of blocking signal transduction pathway of T cells. However, these immunosuppressants are generally accompanied with side effects such as toxicity, infection, lymphoma, diabetes, tremor, headache, diarrhea, hypertension, nausea, and impaired renal function.

Immune disease treatments other than inhibition of T cell activation are also actively researched, which mainly include treatment of regulating amount of cytokine secreted from immune cells, and treatment of using antibody that acts specifically against cytokine secreted from the immune cells. However, these treatments require lengthy times until the treatments are actually made available to patients after clinical trials. The treatment using antibodies also has a drawback, because cost to develop antibodies is extreme.

Accordingly, a new treatment for cancer and immune disease is necessary, which does not have side effect, and is economic and highly effective.

SUMMARY OF THE INVENTION

Technical problems

Accordingly, the present inventors were able to confirm that protein inhibitor of activated signal transducer and activator of transcription (PIAS3) inhibits Th17 activity and increases regulatory T cells (Tregs) activity, and therefore, can be used in all the diseases related with tumor or immunity, and completed the present invention.

Accordingly, an object of the present invention is to provide a composition for preventing or treating cancer of immune disease, comprising PIAS3 gene or protein as an active ingredient to effectively treat various cancers and immune diseases caused due to abnormality in immune response.

Another object of the present invention is to provide a method for decreasing or suppressing in vitro differentiation of non-differentiated T cells into Th17 cells, comprising treating the non-differentiated T cells with PIAS3 gene or protein.

Yet another object of the present invention is to provide a method for activating regulatory T cells, comprising treating in vitro regulatory T cells (Treg) with PiAS3 gene or protein.

Yet another object of the present invention is to provide a composition for immunosuppression, comprising PIAS3 gene or protein as an active ingredient.

Furthermore, yet another object of the present invention is to provide a method of preventing or treating cancer or immune disease comprising administering to a subject in need thereof a pharmaceutical composition comprising isolated PIAS3 (protein inhibitor of activated STAT3) gene or PIAS3 protein as an active ingredient.

Means to Solve the Problems

In order to achieve the above-mentioned objects, the present invention provides a method of preventing or treating cancer or immune disease comprising administering to a subject in need thereof a pharmaceutical composition comprising isolated PIAS3 (protein inhibitor of activated STAT3) gene or PIAS3 protein as an active ingredient.

Also, the present invention provides a composition comprising protein inhibitor of activated signal transducer and activator of transcription (PIAS3) gene or PIAS3 expressing protein as an active ingredient for preventing or treating cancer or immune disease.

In one embodiment of the present invention, the PIAS3 can disease or suppress differentiation of non-differentiated T cells into Th17 cells.

In one embodiment of the present invention, the PIAS3 can promote or enhance activity or expansion of regulatory T cells (Treg).

In one embodiment of the present invention, the cancer may be selected from colon cancer, rectal cancer, anal cancer, bone cancer, stomach cancer, cerebrospinal cancer, head and neck cancer, thymoma, mesothelioma, esophageal cancer, biliary tract cancer, bladder cancer, testicular cancer, small intestine cancer, germ cell tumors, endometrial cancer, fallopian tube carcinoma, vaginal carcinoma, vulva carcinoma, multiple myeloma, sarcoma, adenocarcinoma, endocrine, thyroid cancer, parathyroid cancer, adrenal cancer, bladder cancer, urethral cancer, pituitary adenoma, renal pelvis carcinoma, spinal cord tumors, multiple myeloma, glioma carcinoma, central nervous system tumor, hematopoietic tumor, fibersarcoma, neuroblastoma, astrocytoma, breast cancer, cervical cancer, ovarian cancer, prostate cancer, pancreatic cancer, kidney cancer, liver cancer, brain cancer, lung cancer, lymphoma, leukemia, malignant melanoma and skin cancer.

In one embodiment of the present invention, the immune disease may be selected from a group consisting of autoimmune disease, inflammatory disease, and transplantation rejection of cells, tissues or organs.

In one embodiment of the present invention, the immune disease may be selected from Behcet's disease, multiple myositis/dermatomyositis, autoimmune cytopenia, autoimmune myocarditis, atopic dermatitis, asthma, primary cirrhosis, dermatomyositis, Goodpasteur syndrome, autoimmune meningitis, obesity, Sjogren's syndrome, spastic myelitis, systemic lupus Erythematosus, Addison's disease, alopecia greata, autoimmune hepatitis, mumps, autoimmune insulin-dependent diabetes mellitus, dystrophic epidermolysis bullosa, epididymitis, glomerulonephritis, Graves' disease, Guillain-Barre syndrome, Hashimoto's disease, hemolytic anemia, multiple sclerosis, myasthenia gravis, pemphigus vulgaris, psoriasis, rheumatic fever, rheumatoid arthritis, sarcoidosis, scleroderma, spondyloarthropathy, thyroiditis, vasculitis, vitiligo, myxedema, pernicious anemia, and ulcerative colitis.

Further, the present invention provides a method for decreasing or suppressing in vitro differentiation of non-differentiated T cells into Th17 cells, comprising treating the non-differentiated T cells with PIAS3 gene or protein.

In one embodiment of the present invention, decreasing or suppressing differentiation of the non-differentiated T cells into Th17 may be performed by way of inhibiting production of IL-17 cytokine.

The present invention further provides a method for activating regulatory T cells, comprising treating in vitro regulatory T cells (Treg) with PiAS3 gene or protein.

In one embodiment of the present invention, the activated Treg cells may have increased Foxp3 expression.

Furthermore, the present invention provides a composition for immunosuppression, comprising PIAS3 gene or expressing protein of the gene as an active ingredient.

Effect of the Invention

PIAS3 according to the present invention can be advantageously used as a pharmaceutical composition for preventing or treating various cancers or immune disease such as autoimmune disease caused by abnormality in the regulation of immune response, inflammatory disease and transplant rejection, because PAIS3 has superior inhibitory effect on the differentiation of cytotoxic Th17 cells which generate and secrete inflammatory cytokine, and also has superior promoting effect on the activity of regulatory T cells (Treg) which inhibits function of abnormally-activated immune cells and controls inflammation response.

BRIEF DESCRIPTION OF THE DRAWINGS

The above and/or other aspects and advantages of the present invention will become apparent and more readily appreciated from the following detailed description, taken in conjunction with the accompanying drawings of which.

DETAILED DESCRIPTION OF THE INVENTION

Figure 1:
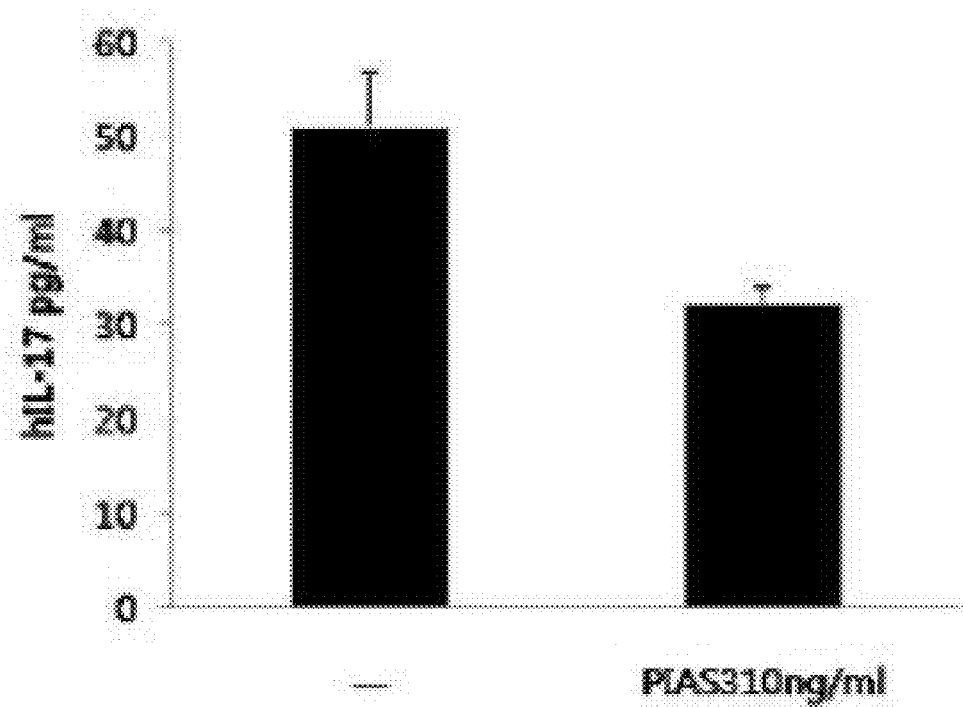
FIG. 1 is a graph illustrating the result of measuring amount of IL-17 cytokine secretion as produced under Th17 differentiation environment after separated CD4+ T cells are treated with PIAS3, according to one embodiment.

The present invention has confirmed for the first time that PIAS3 has the effect of preventing or treating immune disease by way of immunity regulation, and therefore, the present invention provides a composition containing protein inhibitor of activated signal transducer and activator of transcription (PIAS3) gene or PIAS3 expressing protein for preventing or treating cancer or immune disease.

The present inventors particularly focus on PIAS3 gene for the development of new immunosuppressant to treat immune disease. PIAS3, or the protein inhibitor of activated STAT3 is the protein to regulate activity of activated STAT (signal transducer and activator of transcription protein) family member proteins, and is known to regulate activity of various transcription factors such as STAT, NF-kB, SMAD, p53. PIAS regulates transcription activity by various actions including: 1) interfering binding between transcription factor with DNA; 2) involving in the mutual reaction with transcription inhibiting and activating co-factors; or 3) promoting protein sumoylation (involved in the change of protein function and the transcript factor changes capability of transcription pon sumolylation). The recent studies emphasize the role of PIAS in the regulation of immune response.

Meanwhile, the signal transducers and activators of transcription (STAT) protein is activated by extracellular stimulus such as cytokine, hormone, growth factor so that tyrosine residues are phosphorylated, and dimer is formed by the mutual reaction of SH2 domain, which enters into nucleus to be bound to a specific promoter. The signaling of the STAT protein can be controlled by dephosphorlyation and deproteinization.

When the STAT3-related factors were first discussed, PIAS3 and SOCS3 (suppressor of cytokine signaling 3) were discussed as the STAT3 inhibitory feedbacks, and SOCS protein is known to have an inhibitory activity on JAKs to inhibit a ligand-induced response, and PIAS protein is known to have inhibitory activity on STAT3 phosphorylation.

Recently, STAT1, STAT3 and STAT5 in activated forms are discovered in various carcinomas. STAT3 is particularly considered to be an important anticancer target, because STAT3 is activated in not only blood cancer such as leukemia, but also solid cancer such as breast cancer, head and neck cancer, melanoma, ovarian cancer, lung cancer, pancreatic cancer, and prostate cancer.

Further, STAT3 activity includes inhibition of cell apoptosis, inducing of angiogenesis, and inducing of immune privilege. Accordingly, it is possible to control tumor based on complex anticancer mechanism by inhibiting STAT3 activity, and considering the fact that STAT3 protein is involved in various intracellular functions as well as tumors, it is also possible to develop an immunosuppressant by developing STAT3 inhibitor.

Immune system in normal condition generally controls immune response specific to autoantigen, and even suppresses immune response to exterior antigens. Response of pregnant woman to fetus and immune response to microorganism in chronic infection are the examples. These phenomena are the mechanism that can lead to antigen-specific immune tolerance, which are known to be induced by clonal deletion, clonal anergy and active control by regulatory T cells (Treg). Based on the observations on some patients who happen to acquire the immune tolerance to transplant antigen or animal model induced to have immune tolerance as an experiment, it was confirmed that all the three mechanisms mentioned above are involved in the transplant immune tolerance, and particularly, immune regulating T lymphocyte has recently gained attention as the important cells involved in almost all the in vivo immune responses including autoimmune, tumor immune and infection immune responses.

The recently-discovered regulatory T cells, i.e., the regulator T lymphocyte are largely classed into natural Treg and adaptive Treg cells, in which the natural Treg cells, CD4+ CD25+ T cells are acquired with immunosuppressing function as these are newly made in the thymus, and present with 5~10% frequency in peripheral CD4+ lymphocyte of normal entity. Immunosuppressant mechanism of these cells has yet to be elucidated, but it has recently been revealed that Foxp3, the expression regulating factor of the gene, plays an important role in the differentiation and activity of these cells. Further, the peripheral natural T cells can differentiate into cells expressing immunosuppressing effect when stimulated by auto or exterior antigen under specific environment, which are called 'adaptive' or 'inducible' Treg and include Tr1 secreting IL-10 and Th3 and CD8 Ts secreting TGF-β.

As explained above in the Background of the Invention, besides Treg cells, T cells can also differentiate into Th17 cells by differentiation. Th17 cells are made in the presence of TGF-β as Treg cells do, but unlike Treg cells which do not need IL-6, Th17 cells differentiate in the presence of both TGF-β and IL-6 and secret IL-17.

Further, Th17 cells have cytotoxicity which accelerates progress of disease by maximizing signaling of inflammation response. Accordingly, one way to treat cancer or immune disease is to suppress differentiation into Th17 cells or activity thereof.

In consideration of the above, the present inventors investigated if PIAS3 has any effect of treating cancer or immune disease by inhibiting differentiation of the T cells into these pathologic cells 'Th17'. In one embodiment of the present invention, CD4+T cells isolated from human peripheral blood mononuclear cells was treated with PIAS3, incubated under condition for differentiation into Th17, i.e., incubated in the presence of cytokine (e.g., IL-6, IL-21 or IL-23) necessary for differentiation into Th17 cells, and the amount of IL-17, the cytokine produced from Th17 cells, was measured. As a result, it was observed that PIAS3 decreases the amount of IL-17 expressed on t cells (see FIG. 1).

To investigate the above result again, in another embodiment, a recombinant expression vector introduced with PIAS3 was constructed, PIAS3 expression vector was transfected into CD4+ T cells, and the expression of IL-17 and IL-10 according to overexpression of PIAS3 was analyzed. As a result, compared to the cells transfected with control vector without PIAS3 inserted therein, the cells overexpressing PIAS3 due to PIAS3 expressing vector had decreased expression of IL-17, while the cells had increased expression of IL-10, the cytokine expressed on Treg cells (see FIGS. 6 and 7).

Further, in another embodiment of the present invention, CD4+ T cells separated from human peripheral blood mononuclear cells was treated with siRNA PIAS3 to knock down the PIAS3 gene in the cells and thus inhibit expression, incubated under condition for differentiation into Th17 cells, and amount of IL-17, the cytokine produced from Th17 cells, was measured. As a result, compared to a control in which siRNA PIAS3 is not introduced into the cells, the amount of produced IL-17 increased (see FIG. 2). Accordingly, on reviewing the above-mentioned results, the present inventors was able to confirm the fact that PIAS3 gene or PIAS3 protein according to the present invention act to inhibit or decrease differentiation of non-differentiated T cells into Th17 cells, and furthermore inhibits differentiation into Th17 cells via inhibition of IL-17 production via STATS.

The PIAS3 gene or expressing protein of the gene according to the present invention has a characteristic of preventing or treating cancer or immune disease by an action of decreasing or suppressing the differentiation of non-differentiated T cells into pathologic cells 'Th17' cells. That is, according to the present invention, prevention or treatment of cancer or immune disease is possible via immunosuppression.

The prevention or treatment effect of PIAS3 on immune disease was also confirmed via animal test according to one embodiment of the present invention. That is, mock vectors, in which PiAS3 expression vector and PIAS3 were not introduced, were injected to mouse with induced arthritis by type II collagen, respectively, and arthritis index and joint damage were analyzed. As a result, mouse injected with PIAS3 expression vector to overexpress PIAS3 showed improvement in the symptoms of arthritis compared to a control (see FIG. 8a), greatly reduced inflammatory response and cartilage damage than the control (see FIG. 8b), and also greatly reduced infiltration of inflammatory cells in the articular tissue (see FIG. 8c).

Figure 9:
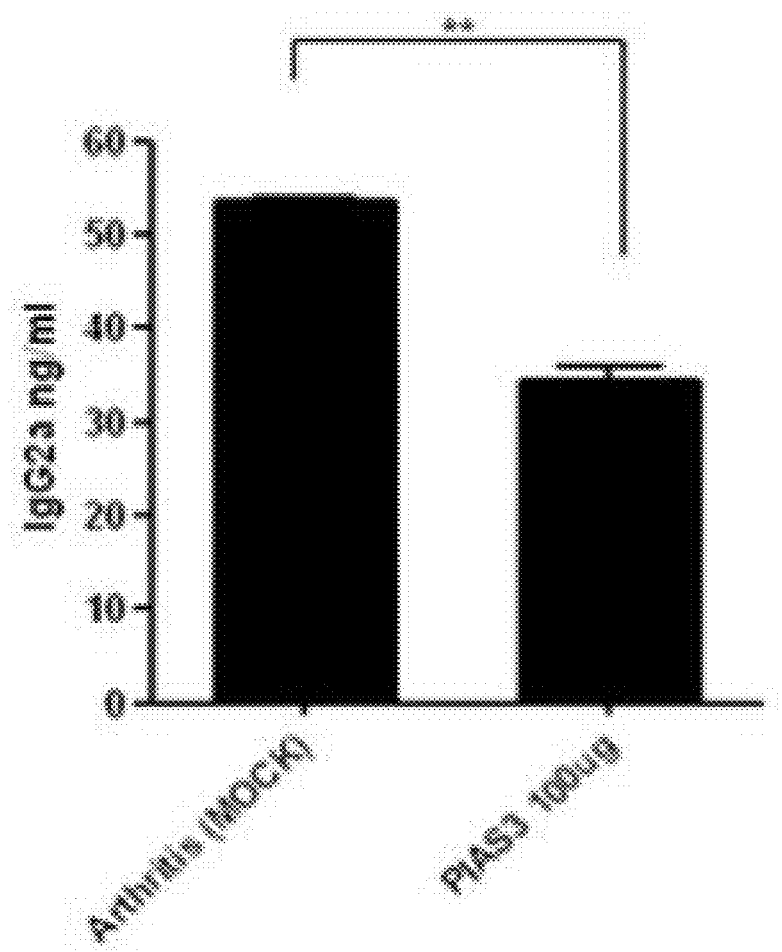
FIG. 9 illustrates the result of measuring by ELISA the amount of IgG2a expression present in serums of the respective mouse induced with arthritis with type II collagen and receive injection of PIAS3 expression vector and the control expression vector.

Furthermore, as a result of isolating serum from the respective mouse groups of the above mouse models and analyzing IgG2a expression present in the serum with ELISA, it was observed that the group with PIAS3 overexpression had decreased IgG2a expression than the control (see FIG. 9).

Figure 10:
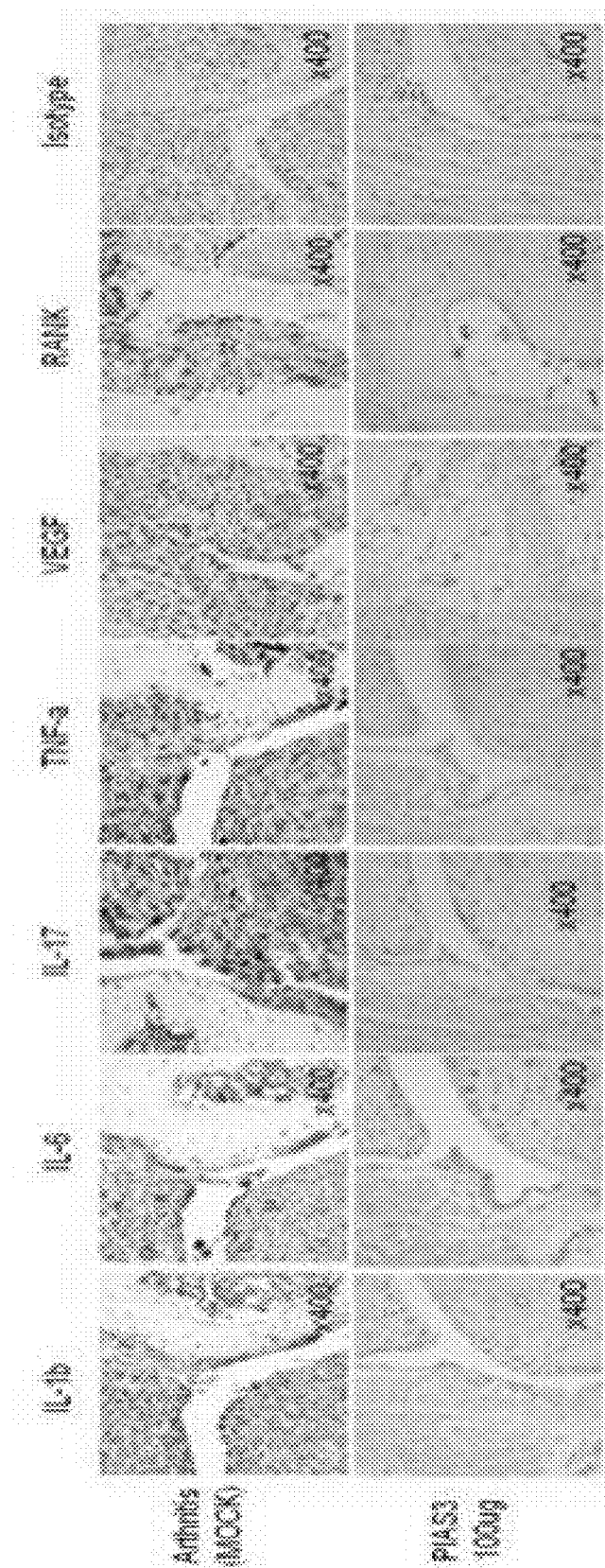
FIG. 10 is an image showing the level of expression of IL-1b, IL-6, IL-17, TNF-a, VEGF, RANK by immunohistochemical staining using corresponding antibodies on the articular tissues sampled from the respective mouse induced with arthritis with type Ii collagen and receive injection of PIAS3 expression vector and the control expression vector.

Further, in another embodiment, arthritis mouse model injected with PIAS3 expression vector had decreased secretion of IL-1b, IL-6, TNF-a, the inflammatory cytokines, compared to those injected with a control vector (i.e., mock vector in which PIAS3 is not introduced), and RANK, the articular damage factor, and VEGF, the angiogenesis factor, were also greatly reduced (see FIG. 10). From the above findings, it was possible to confirm that the PIAS3 according to the present invention can actually treat and prevent immune disease by suppressing inflammatory cytokines in the cells with arthritis and by suppressing infiltration and proliferation of inflammatory cells.

Further, to investigate possible influence of PIAS3, which has production inhibitory effect on IL-17 via STAT3, on Treg cells, in one embodiment, non-differentiated T cells were treated with PIAS3, and incubated under condition for differentiation into Th17 cells. As a result of observing expression of Foxp3 gene in Treg cells, the present inventors were able to confirm that the cells treated with PIAS3 had increased Foxp3 gene expression compared to the non-treated control (see FIG. 3). Further, PIAS3 gene was knocked down in cells with the treatment of siRNA PIAS3. After incubation under condition for differentiation into Th17 cells, the expression of Foxp3 of Treg cells was observed. The observation revealed that Foxp3 gene expression was reduced by the PIAS knockdown by more than half compared to the control (see FIG. 4).

In one embodiment of the present invention, to investigate activation of regulatory T cells (Treg) by PIAS3, the inventors measured Foxp3 gene expression according to PIAS3 treatment. This is in consideration of the fact that the Foxp3 is mainly present in the regulatory T cells originated from thymus and is the transcriptional factor present in CD4+ CD25+ antigen-presenting cells with a function of a suppressor T cell which suppresses production of IL-2 and cell division regarding the T cells that can potentially induce autoimmunity among thymus-originated-Foxp3-non-expressing CD4+ CD25- T cells. Further, it is reported that Foxp3 functions to suppress transcriptional regulation of not only IL-2, but also IL-4, IFN-gamma, etc. which are influenced by the transcriptional factor NFAT concerning Foxp3-expressing Treg cells and CD25-T cells via cell-cell contact. Accordingly, the Foxp3-expressing T cells with the above activity are applied for the treatment of immune disease in view of immunosuppressive or regulative action thereof. Further, attempts have been made to provide cell therapy by increasing the number of self-antigen specific T cell clones of Foxp3-expressing CD4 T cells present in human with the treatment of high concentration of IL-2 cytokine and combined treatment of anti-CD3 and anti-CD28 antigens.

Accordingly, from the finding obtained as a result of one embodiment of the present invention, the inventors were able to confirm that Foxp3 expression increased in PIAS3-treated Treg cells, and thus confirm that PIAS3 according to the present invention can be used for the prevention or treatment of cancer or immune disease via activation or expansion of Treg cells.

Figure 12:
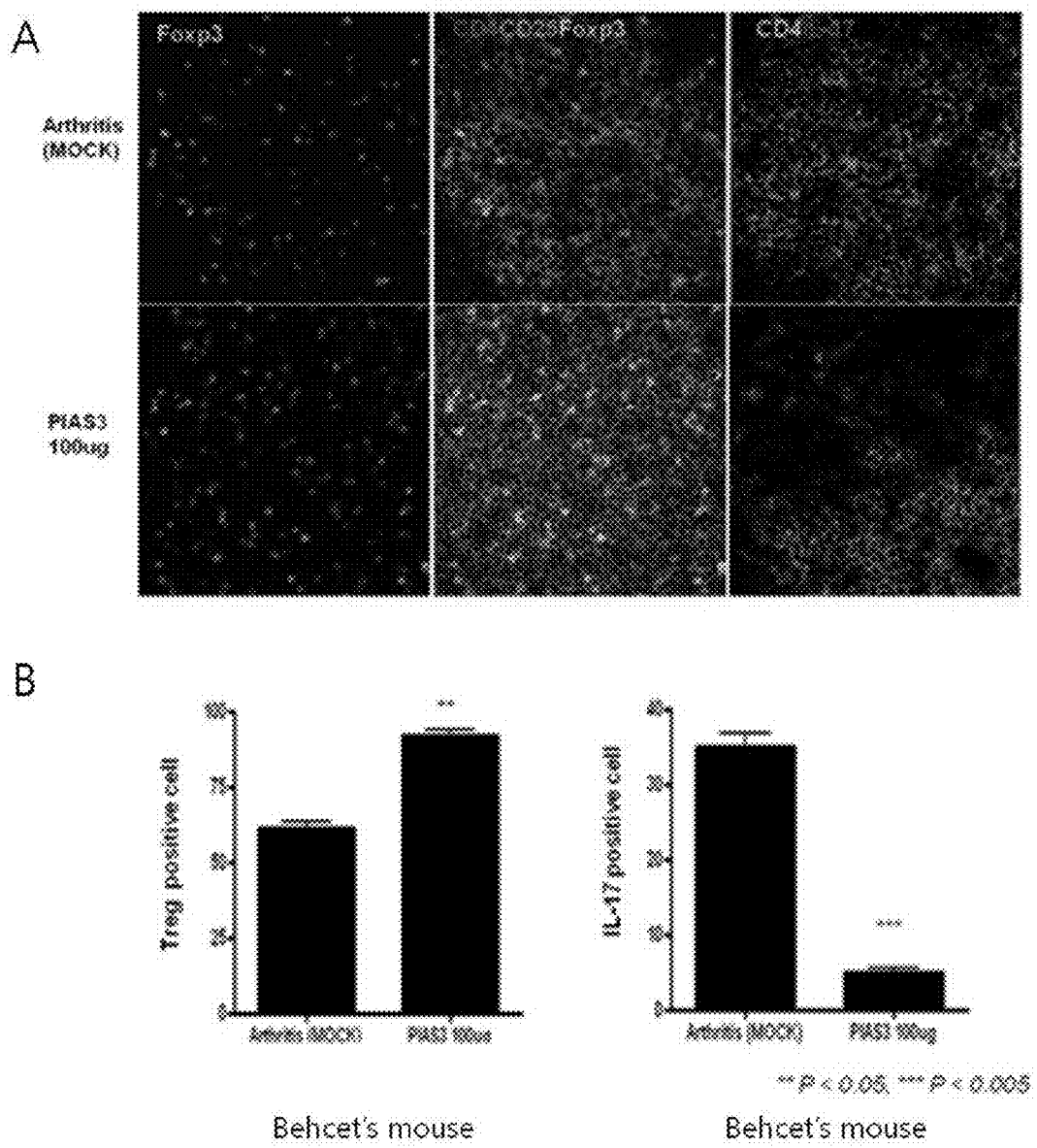
FIG. 12a is a photograph by cofocal staining of cells expressing Foxp3 and IL-17 in the tissues of the spleen separated from the mouse which are induced with Behcet's disease and receive injection of PIAS3 expression vector, compared to a control injected with the mock vector.
FIG. 12b is a graph illustrating the result of counting and comparing the number of Treg positive cells and IL-17 positive cells as observed through the cofocal staining.

Further, such pharmacological effect of PIAS3 was confirmed through the Behcet's disease-induced animal model. That is, in one embodiment of the present invention, mouse with Behcet's disease infected with HSV received PIAS3 expressing vectors and mock vectors injections respectively. Spleen tissues were separated from the respective mouse groups, and Foxp3 and Treg expressing cells and IL-17 positive cells of the spleen tissues were analyzed through confocallaser scanning microscope (CLSM). As a result, PIAS3 expressing vector-injected mouse group had increased Foxp3 and Treg expressions compared to the control mouse group, while IL-17 positive cells were reduced (FIGS. 12a and 12b).

Accordingly, the PIAS3 gene or the PIAS3 gene expressing protein according to the present invention has a characteristic of preventing or treating cancer or immune disease by the activity to promote or increase activity or expansion of Treg cells.

The "activity" as used herein refers to promoting or enhancing of all the mechanisms of the Treg cells, including both natural Treg and adaptive Treg cells, and it also refers to promoting or enhancing of immune regulating action, e.g., immunosuppressive response, to keep the immune response in a body under normal condition.

Further, the "expansion" as used herein refers to differentiation and proliferation of non-differentiated T cells into Treg cells, in which the "differentiation" as used herein refers to a phenomenon that the cells have specified structure or functions along the process of division, proliferation and growth, that is, to varying of cells or tissues of a living organism the shapes or functions thereof to get to respectively-given jobs, and "proliferation" refers to homogenous cells increasing in number by division, and usually refers to the increase of cell numbers in a body of multicellular organism.

Accordingly, the present invention provides a composition comprising PIAS3 gene or PIAS3 gene expressing protein as an active ingredient for the prevention or treatment of cancer or immune disease, and the PIAS3 gene according to the present invention may preferably be a gene with sequence represented by SEQ ID NO: 1.

Further, the PIAS3 protein according to the present invention may be functional equivalent to a polypeptide with amino acid sequence represented by SEQ ID NO: 1. The "functional equivalent" as used herein refers to polypeptide with substantially same quality of activity as PIAS3 according to the present invention, which may have sequence homology of at least 60%, preferably 70%, and more preferably 80% or above to the amino acid sequence expressed by SEQ ID NO: 1 as a result of addition, substitution or deletion of amino acid. The "substantially similar quality of activity" as used herein refers to the activity of PIAS3 as described above. The functional equivalent may include sequence variant having part of amino acid of amino acid sequence represented by SEQ ID NO: 1 being substituted, deleted or added. The substitution of amino acid may preferably be conservative substitution, and example of naturally-occurring conservative substitution of amino acid includes: aliphatic amino acid (Gly, Ala, Pro), hydrophobic amino acid (Ile, Leu, Val), aromatic amino acid (Phe, Tyr, Trp), acidic amino acid (Asp, Glu), basic amino acid (H is, Lys, Arg, Gln, Asn) and sulfur bearing amino acid (Cys, Met). The "deletion" of amino acid may be at a site which is not directly involved with the activity of PIAS3 according to the present invention. Further, the functional equivalent may include in its scope polypeptide derivatives with maintained Grim19 skeleton and biological activity, and partially altered chemical structure of polypeptide. For example, fusion protein of different proteins, which maintains altered structure to vary stability, preservativeness, volatility or solubility, and biological activity of the original polypeptides.

The PIAS3 gene or the PIAS3 gene expressing protein according to the present invention can prevent or treat cancer or immune disease via action of decreasing or suppressing pathological cell Th17, and promoting or increasing activity or expansion of Treg cells.

The "cancer" as used herein is defined as a disease with abnormally fast and uncontrollable growth of cells. The cancer cell can spread locally or migrate to the other part of the body along bloodstream and lymphatic system. Further, throughout the description, the type of the cancer may include, but not limited to, colon cancer, rectal cancer, anal cancer, bone cancer, stomach cancer, cerebrospinal cancer, head and neck cancer, thymoma, mesothelioma, esophageal cancer, biliary tract cancer, bladder cancer, testicular cancer, small intestine cancer, germ cell tumors, endometrial cancer, fallopian tube carcinoma, vaginal carcinoma, vulva carcinoma, multiple myeloma, sarcoma, adenocarcinoma, endocrine, thyroid cancer, parathyroid cancer, adrenal cancer, bladder cancer, urethral cancer, pituitary adenoma, renal pelvis carcinoma, spinal cord tumors, multiple myeloma, glioma carcinoma, central nervous system tumor, hematopoietic tumor, fibersarcoma, neuroblastoma, astrocytoma, breast cancer, cervical cancer, ovarian cancer, prostate cancer, pancreatic cancer, kidney cancer, liver cancer, brain cancer, lung cancer, lymphoma, leukemia, malignant melanoma and skin cancer.

The "immune disease" as used herein refers to a disease in which constituents of mammalian immune system induce, mediate or contribute in anyway to pathological condition. Further, the immune disease may encompass any diseases in which stimulus or stopping of immune response have compensatory effect on the progress of such diseases. According to the present invention, the immune disease may include all the diseases caused by hypersensitive immune response. An example of the immune disease may include, but not limited to: autoimmune disease; inflammatory disease; and transplantation rejection of cells, tissues or organs.

One of the most important characteristics of a normal entity is an ability to recognize and respond to non-self antigens, while not responding harmfully to self-antigens. This non-responding of a living organism to self-antigens is called "immunologic unresponsiveness" or "tolerance".

When this ability to induce or maintain self tolerance is troubled, immune response occurs even to the self antigens, leading to a phenomenon of attacking self tissues, and autoimmune disease is developed in this process.

Further, the "inflammatory disease" as used herein refers to a disease which is caused by the inflammation inducing substance (inflammatory cytokine) such as TNF-α (tumor necrosis factor-α), IL-1 (interleukin-1), IL-6, prostaglardin, luecotriene or nitric oxide (NO) secreted from immune cells such as macrophage due to excessive acceleration of immune system of a human body in response to hazardous stimulus such as inflammation inducing factor, radiation, or the like.

Meanwhile, immunological rejection of a recipient to the transplanted cells or organs has to be dealt with, in order to ensure successful organ transplant. T cells are the major mediator of transplantation rejection. That is, immune response is induced, leading to transplantation rejection, as the T cell receptor perceives the major histocompatibility complex (MHC) expressed on the graft. Immunosuppressants are used to decrease the transplantation rejection. The common purpose of these immunosuppressants is to suppress T cell-mediated immune response to the graft, and new attempts have recently been adopted to treat transplantation rejection by suppressing immune response using Treg cells.

Further, an example of the immune disease according to the present invention may include, but not limited to: Behcet's disease, multiple myositis/dermatomyositis, autoimmune cytopenia, autoimmune myocarditis, atopic dermatitis, asthma, primary cirrhosis, dermatomyositis, Goodpasteur syndrome, autoimmune meningitis, obesity, Sjogren's syndrome, spastic myelitis, systemic lupus Erythematosus, Addison's disease, alopecia greata, autoimmune hepatitis, mumps, autoimmune insulin-dependent diabetes mellitus, dystrophic epidermolysis bullosa, epididymitis, glomerulonephritis, Graves' disease, Guillain-Barre syndrome, Hashimoto's disease, hemolytic anemia, multiple sclerosis, myasthenia gravis, pemphigus vulgaris, psoriasis, rheumatic fever, rheumatoid arthritis, sarcoidosis, scleroderma, spondyloarthropathy, thyroiditis, vasculitis, vitiligo, myxedema, pernicious anemia, and ulcerative colitis.

Accordingly, the composition according to the present invention can be used as a pharmaceutical composition for the prevention or treatment of cancer or immune disease. Unless otherwise specified, the expression "treatment" as used herein refers to reversing, relieving, or suppressing progress, or preventing a disease or ailment to which the expression is applied or one or more symptoms thereof, and the expression "treatment" as used herein refers to an act of treating as defined above. Accordingly, a treatment or therapy of cancer or immune disease of a mammalian animal includes one or more of the following:

(1) inhibiting growth of cancer or immune disease, that is, impeding development thereof;

(2) preventing proliferation of cancer or immune disease, that is, preventing spreading;

(3) relieving cancer or immune disease;

(4) preventing recurrence of cancer or immune disease; and (5) palliating symptoms of cancer of immune disease.

A composition for preventing or treating cancer or immune disease according to the present invention may include a pharmaceutically effective amount of PIAS3 gene or PIAS3 expressing protein either singly or in combination with one or more pharmaceutically acceptable carrier, excipient or diluent. The "pharmaceutically effective amount" as used herein refers to an amount sufficient to prevent, improve and treat symptoms of cancer of immune disease.

The pharmaceutically effective amount of PIAS3 gene or the PIAS3 expressing protein according to the present invention is 0.5~100 mg/day/weight (kg), and preferably, 0.5~5 mg/day/weight (kg). The pharmaceutically effective amount may vary appropriately, depending on severity of symptom of immune disease, age, weight, health condition, gender, route of administration and period of treatment of a patient.

Further, the "pharmaceutically acceptable" as used herein refers to a biologically acceptable composition which, when administered to human, does not raise allergic reaction such as gastroenteric trouble or dizziness, or similar reaction. An example of the carrier, exipient and diluent includes lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methyl hydroxybenzoate, propyl hydroxybenzoate, talc, magnesium stearate, and mineral oil. Further, filler, antiagglomerating agent, lubricant, wetting agent, fragrance, emulsifier and preservative may additionally be included.

Further, the composition according to the present invention may be formulated into a dosage form according to a known method to provide rapid, continuous or delayed release once administered into a mammalian animal. The dosage form may include a form of powder, granule, tablet, emulsion, syrup, aerosol, soft or hard gelatin capsule, sterile injection solution, or sterile powder.

Further, the composition for preventing or treating cancer or immune disease according to the present invention may be administered via various routes including oral, percutaneous, subcutaneous, intravenous or intramuscular route, and an administered amount of an active ingredient may be appropriately selected depending on the route of administration, and age, gender, weight and severity of a patient. The composition for preventing or treating cancer or immune disease according to the present invention may be administered along with a known compound with effect of preventing, improving or treating symptoms of cancer or immune disease.

Accordingly, the present invention provides a medicament comprising PIAS3 gene or PIAS3 expressing protein as an active ingredient for preventing or treating cancer or immune disease, and furthermore, provides a composition comprising PIAS3 gene or PIAS3 expressing protein as an active ingredient.

Further, the present invention provides a method for reducing or suppressing differentiation of non-differentiated T cells into Th17 cells in vitro, comprising treating the non-differentiated T cells with PIAS3 gene or PIAS3 expressing protein, in which reduction or suppression of the differentiation of the non-differentiated T cells into Th17 cells may be performed via suppression of production of IL-17 cytokine.

Further, the present invention provides a method for activating Treg cells, comprising treating Treg cells with PIAS3 gene or PIAS3 expressing protein in vitro, according to which the activated Treg cells may have increased Foxp3 expression.

In a method for decreasing or suppressing differentiation of non-differentiated T cells into Th17 in vitro, or a method for treating PIAS3 gene or PIAS3 expressing protein to cell may involve direct treatment of the PIAS3 protein on the cell culture media, or expressing PIAS3 gene in the cells by introducing an expression vector of gene encoding PIAS3 protein using a known method such as a method of using $Ca^{2+}(CaCl_2)$ into the cells.

According to the present invention, the PIAS3 gene contains DNA sequence encoding the PIAS protein or functional equivalent thereof, in which the DNA sequence may encompass DNA, cDNA and RNA sequences, and preferably be the DNA sequence encoding amino acid sequence of SEQ ID NO: 1.

Furthermore, the PIAS3 protein used in the present invention may be prepared by the DNA recombinant technology, using known methods. To be specific, it is possible to prepare the PIAS3 protein using genetic engineering which introduces the PIAS3 gene in germs, yeast, plant cell cultures and animal cell cultures with a recombination method. Alternatively, the PIAS3 protein may be prepared by purifying and isolating naturally-expressed PIAS3 protein in the cells using known protein purification and isolation method. However, since the above are given only for illustrative purpose, a method for preparing the PIAS3 protein and treating the protein on the cells is not limited to the specific examples given above.

The present invention will be explained in further detail with reference to examples. However, one will appreciate that these examples are given only for illustrative purpose, and cannot be construed as limiting the scope of the present invention.

EXAMPLE 1

Analysis of IL17 Production Inhibitory Activity of Th17

To investigate whether PIAS3 protein has an effect of treating cancer or immune diseases, the inventors measured changes in 11-17 cytokine secretion by PIAS3 in Th17 involved with these diseases. To this end, Th17 were differentiated and separated from CD4+ T.

<1-1> Isolation of CD4+ T

To separate CD4+T, blood sample was taken with heparin-treated needle from a healthy subject, and peripheral blood mononuclear cells (PBMC) were separated with Ficoll-Paque™ using centrifuge gradient. The separated PBMC were left reacted in anti-human CD4+T biotin-Ab cocktail at 4° C., 15 m, reacted with anti-human CD4 biotin microbead at 4° C., 15 m, washed with MACs buffer, and then CD4+T was separated with autoMACs by negative selection. The separated CD4+T was washed with PBS, and incubated at 55° C., 30 m, in cell culture (RPMI1640 medium, Gibco BRL, USA) containing inactivated 10% fetal bovine serum (FBS), penicillin (100 U/mL) and streptomycin (100 g/mL).

<1-2> Treatment of Recombinant PIAS3

CD4+T separated from human PMBC ($5 \times 10^5$) and antigen presenting cells (APC) radiated at 5000 rad ($5 \times 10^5$) were incubated in 1 mL of 10% RPMI, and the cells were treated with 10 ng/mL concentration of recombinant PIAS3, the inhibitor of STAT3, and incubated for 24 h.

<1-3> Cell Stimulation $5 \times 10^5$ of CD4+T separated from human PMBC and treated with PIAS3 at Example <1-2> and $5 \times 10^5$ of APC radiated at 5000 rad were seeded in 1 μg/mL anti-CD3-coated 24 well plate, and treated with 1 μg/mL of anti-CD28 antigen and 10 ng/mL of IL-6 20 ng/mL, IL-1β 20 ng/mL, IL-23 20 ng/mL, anti-IL-4 10 ng/mL and anti-IFNr, to induce differentiation into Th17.

<1-4> Measurement of IL-17 Cytokine (ELISA)

In order to measure the amount of produced IL-17 cytokine, the supernatant of the cell culture medium was collected and level of IL-17 expression was investigated using human IL-17 and sandwich ELISA. After reaction on a 96 well plate with 2 μg/mL of monoclonal anti-IL-17 at 4° C., overnight, non-specific binding was blocked with blocking solution (1% BSA/PBST). Recombinant IL-17 was successively diluted by ½ each and used as a standard measure, and the cell culture supernatant was reacted at room temperature, 2 h. After that, biotinylated anti-IL-17 was reacted at room temperature, 2 h, washed four times, and then ExtraAvidin-Alkaline Phosphatase conjugate was diluted and added. After reaction at room temperature for 2 h, PNPP/DEA solution was added and converted into color. Accordingly, absorbency was measured at 405 nm wavelength.

As a result, referring to FIG. 1, it was observed that PIAS3 decreases IL-17 cytokine production in T cells. Based on the above observation, it was confirmed that PIAS3 inhibits Th17 activity and secretion of IL-17 cytokine.

EXAMPLE 2

Analysis of IL-17 Production Inhibitory Activity in Cells by siRNA PIAS3

To further investigate whether the PIAS3 has an activity to inhibit IL-17 cytokine secretion in Th17 induced to differentiate from CD4+ T cells at <Example 1>, the inventors prepared siRNA type of PIAS3 inhibitor and treated cells with the siRNA and observed variations in the IL-17 expression.

First, CD4+ T cells were separated in the same manner as explained at Example <1-1>, and before inducing differentiation of CD4+ T to Th17, the cells were treated with siRNA for PIAS3 knockdown. That is, the separated CD4+T ($5 \times 10^5$) was incubated at serum-free RPMI medium, and treated with siRNA PIAS3 and reagent conjugate for 48 h to thus knock down PIAS3 gene.

After that, $5 \times 10^5$ of PIAS3-knockdown CD4+ T cells of Example <1-3>과 and $5 \times 10^5$ of APC radiated at 5000 rad were incubated under cell differentiating cytokine environment, i.e., on a medium containing the above-explained cytokines. After 48 h, the amount of IL-17 cytokines was measured on the culture broth. For control, siRNA PIAS3-excluded transfected reagent was treated.

To measure the amount of produced IL-17 cytokines, in the same manner of Example <1-4>, the supernatant of the cell culture medium was collected and the level of IL-17 expression was analyzed using human IL-17 and sandwich ELISA.

Figure 2:
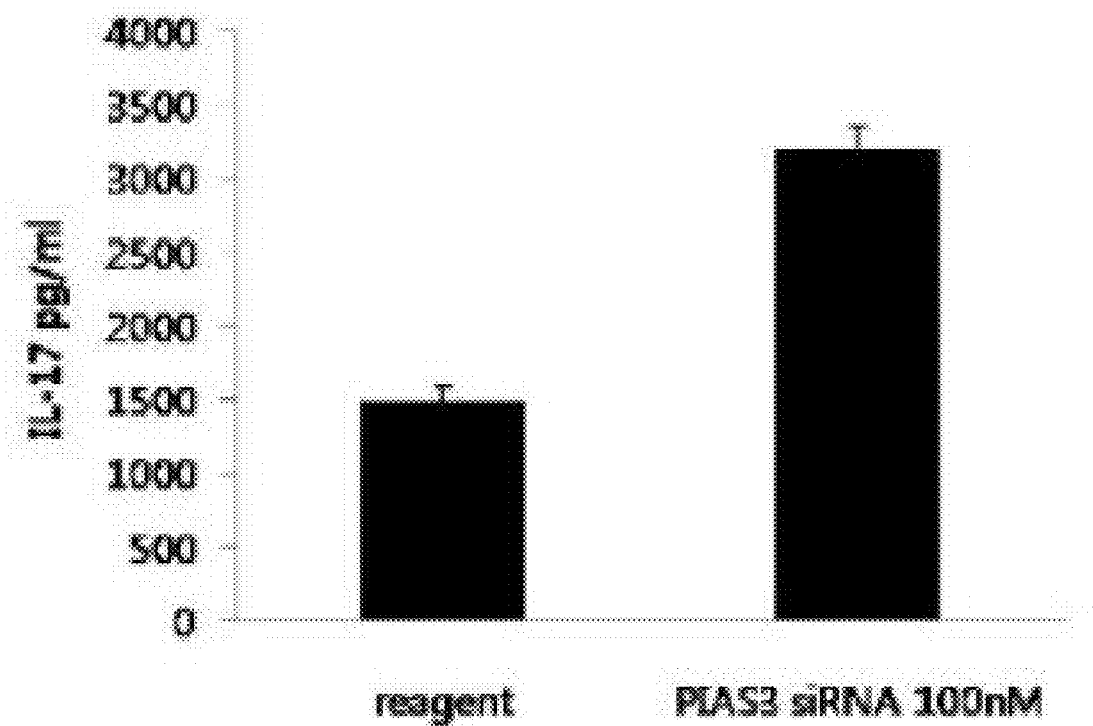
FIG. 2 is a graph illustrating the result of measuring amount of IL-17 cytokine secretion as produced under Th17 differentiation environment after separated CD4+ T cells are treated with siRNA PIAS3, according to one embodiment.

As a result, referring to FIG. 2, the group with PIAS3 knocked down with siRNA PIAS3 showed increased production of IL-17 cytokines than control. From the above observation, it was once again confirmed that PIAS3 can inhibit the expression level of IL-17.

Accordingly, based on the findings of <Example 1> and <Example 2>, the inventors were able to confirm that PIAS3, the inhibitor of STAT3, can inhibit production of IL-17 cytokines. Further, considering the activity of PIAS3 to inhibit IL-17 cytokine production via STAT3 in the Th17 which is accepted to be crucial cells involved with neutrophil activity and inflammatory cytokine and chemokine production, the inventors were able to anticipate that PIAS3 can prevent or treat various inflammatory diseases, immune diseases and cancers with the activity of inhibiting IL-17 cytokine production via STAT3.

EXAMPLE 3

Analysis of PIAS3 Influence in Treg

General understanding is that the regulatory T lymphocytes (Treg) play a central role in the maintenance of immune tolerance, that Treg are mainly produced from thymus requiring expression of Foxp3 as the transcriptional factor, and that Foxp3 also plays the role or inhibiting production of inflammatory cytokines. It is also reported that Tr1, the cells producing IL-10 in Treg, remove T cell action and inflammation of the tissue without having Foxp3 expression. In consideration of the above, the inventors analyzed expression level of Foxp3 of the cells underwent PIAS3-treated Th17 differentiation environment, and analyzed Foxp3 expression at mRNA level with RT-PCR.

First, under Th17 differentiation condition, cells were treated with 10 ng/ml PIAS3, RNA was extracted from the cells by known methods and cDNA products were obtained. Using cDNA products, polymerase chain reaction (PCR) was conducted using primers to expand human Foxp3 and β-actin (control). RT-PCR was conducted with cDNA reverse-transcribed at different amounts during amplification and varying amplification fold, and the logarithmically increasing cDNA amount and the amplification fold were determined.

The reaction compound for RT-PCR was total 25 μl, and the solution composition included 2.5 μl 10× reaction buffer, 0.5 mM of dNTP, and respective primer pairs of sequences of Table 1. Dual-bay Thermal cycler system was used for amplification, with a cycle of denaturalization 94° C., 30 s, annealing 60° C., 30 s, and elongation 72° C., 30 s, repeated 25 times.

TABLE 1

| Primer | Primer sequence | SEQ ID NO. |
|---|---|---|
| Foxp3 sense | 5-ATGCCTCCTCTTCTTCCTTGA-3 | 2 |
| Foxp3 antisense | 5-TGAGAAGGGCAGGGCACAAT-3 | 3 |
| -actin sense | 5-GGACTTCGAGCAAGAGATGG-3 | 4 |
| -actin antisense | 5-TGTGTTGGCGTACAGGTCTTTG-3 | 5 |

Figure 3:
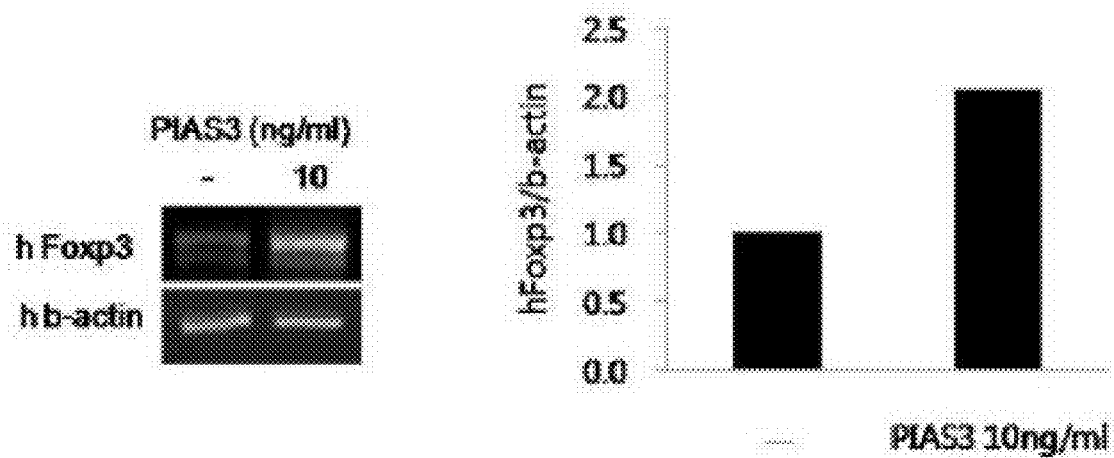
FIG. 3 is a graph illustrating the result of measuring and comparing the levels of Foxp3 expression in cells by RT-PCR, in which the separated CD4+ T cells are treated with 10 ng/ml concentration of PIAS3, according to one embodiment.

As a result, referring to FIG. 3, the cells treated with PIAS3 at 10 ng/mL concentration showed two-fold increase of Foxp3 expression than the control.

EXAMPLE 4

Analysis of siRNA PIAS3 Influence in Treg

To further investigate whether PIAS3 has an activity to increase Foxp3 expression as explained above at <Example 3>, PIAS3 inhibitor was prepared into siRNA type as explained at <Example 2>. After treating the cells with the prepared siRNA, changes in the Foxp3 expression were measured in the same manner as <Example 3>.

Figure 4:
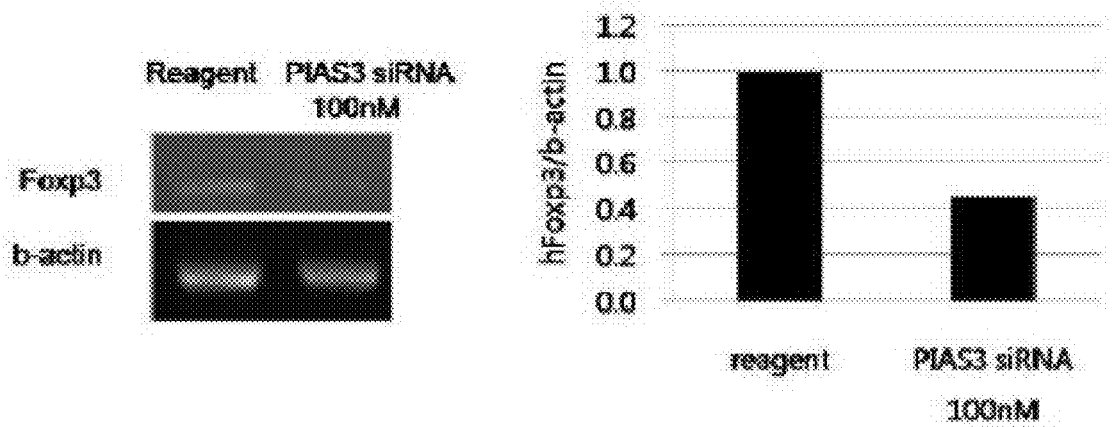
FIG. 4 is a graph illustrating the result of measuring and comparing the levels of Foxp3 expression in cells by RT-PCR, in which the separated CD4+ T cells are treated with 10 ng/ml concentration of siRNA PIAS3, according to one embodiment.

As a result, referring to FIG. 4, the Foxp3 expression by the PIAS3 knockdown reduced more than by half, compared to the control.

Accordingly, in consideration of the findings of <Example 3> and <Example 4>, the inventors were able to confirm that PIAS3, the STAT3 inhibitor, has an effect of increasing Foxp3 expression.

Lastly, from the above findings, the inventors were able to confirm that PIAS3 according to the present invention inhibits cell differentiation into Th17 via inhibition of STAT3 action, while increasing the Foxp3 expression. As a result, the inventors were able to confirm that PIAS3 can enhance, prevent or treat symptoms of cancer or immune disease via regulation of immune response by regulating T cells.

EXAMPLE 5

Analysis of Influence of PIAS3 Overexpression on IL-17 and IL-10 Production

In the above examples, the inventors confirmed the effect of PIAS3 on the production of IL-17 and IL-10 using siRNA. In this example, the inventors confirmed the effect of PIAS3 overexpression on the production of IL-17 and IL-10. That is, to prepare an expression vector to overexpress PIAS3, PIAS3 cDNA clone was purchased from 21C Human Gene Bank, and cut into restriction enzymes Kpn 1 and Xho 1, and inserted into pcDNA3.1+(promega). E. coli was transfected with the recombinant vector plasmid and incubated, the recombinant vector plasmid was isolated from the E. coli with the Plasmid Extraction kit (Qiagan). After electrophoresis, amount of DNA was analyzed using nanodrop, and the sequence of the recombinant gene was analyzed to confirm if the orientation of PIAS3 insertion into pcDNA3.1+ (promega) vector and the sequence were accurate. Accordingly, recombinant PIAS3-transfected plasmid vector was separated. To investigate if the PIAS3 is overexpressed due to the prepared vector, the PIAS3-inserted expression vector plasmid was transfected into NIH3T3 cell line, with Polymag (Chemicell) diluted 10-fold in serum free RPMI, and the PIAS3 expression vector (1 ug) added. The mixture was left at room temperature for 30 min, reacted with magnetoplate for 5 min and transfected into NIH3T3 cell line. After incubation for 2 days, the cell lysate was obtained, and western blotting was conducted using antigens by PIAS3 purchased from Sigma as instructed by the antigen provider. For control, empty vector (no vector insert) was used in the same experiment.

Figure 5:
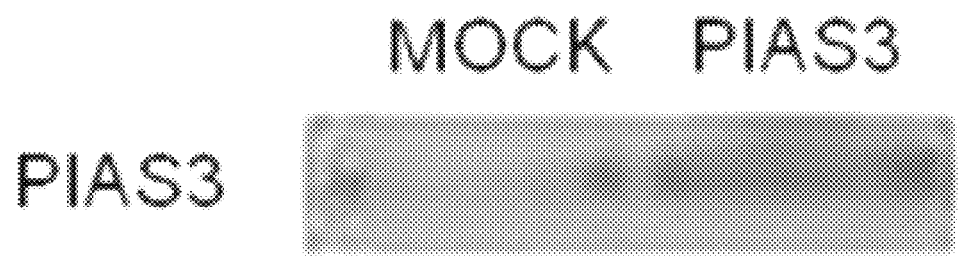
FIG. 5 illustrates the result of Western blot analyzing the amount of PIAS3 expressed within cells, after PIAS3-inserted recombinant expression vector and mock vector (no PIAS3 insert) as a control are transfected into NIH3T3 cells.

As a result, referring to FIG. 5, the expression vector with PIAS3 insert had PIAS3 overexpression compared to a control using empty vector (no PIAS3 insert), and therefore, it was confirmed that the PIAS expressing vector prepared in the manner explained above can overexpress PIAS3 in the cells as intended.

Next, the inventors separated mouse CD4+ T using MACs beads, transfected the PIAS3 expression vector into CD4+ T in the same manner as explained above, except for transfecting the vector into CD4+ T instead of NIH3T3 cell line. After one day, Th17 differentiation condition, that is, anti-CD28 antibody (1 g/mL) and IL-6 (20 ng/mL), IL-1β (20 ng/mL), IL-23 (20 ng/mL), anti-IL-4 (10 ng/mL) and anti-IFNr (10 ng/mL) were treated on the cell lysate, thus differentiating the cells to Th17. The level of IL-17 mRNA expression was then analyzed by real-time PCR, and for the control, the mock vector (no PIAS3 insert) was added instead of PIAS3 expression vector. The real-time PCR was conducted to confirm the expression of IL-17 gene, using the primer sequences listed below, and the result was analyzed using SYBR Green I (Roche Diagnostic, Mannheim, Germany) and Light Cycler instrument (Roche Diagnostic).

TABLE 2

Primer sequence

| Primer | Primer sequence | SEQ ID NO. |
|---|---|---|
| IL-17 sense | 5-CCTCAAAGCTCAGCGTGTCC-3 | 6 |
| IL-17 antisense | 5-GAGCTCACTTTTGCGCCAAG-3 | 7 |
| β-actin sense | 5-GAAATCGTGCGTGACATCAAAG-3 | 8 |
| β-actin antisense | 5-TGTAGTTTCATGGATGCCACAG-3 | 9 |

Further, flow cytometry was conducted to analyze the expression level of IL-10. Regarding the CD4+ T cells transfected with the PIAS3 expression vector and the CD4+ T cells transfected with the control vector, the cytokine antibodies with fluorescence attached to the above cells, that is, the cells were treated with IL-10 specific antibodies, and the CD4 antibodies with different fluorescence at the same time are bound to the cells, and the cells expressing IL-10 cytokines were analyzed using flow cytometry.

Figure 6:
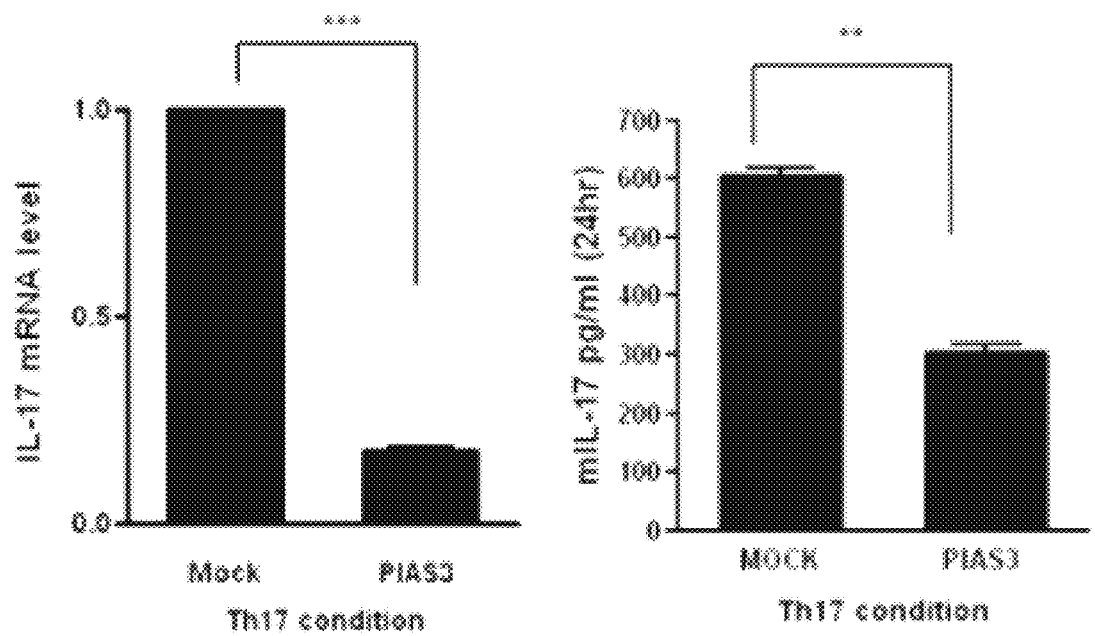
FIG. 6 is a graph illustrating the result of measuring amount of IL-17 secreted from cells using amount of IL-17 mRNA and ELISA to confirm the level of IL-17 expression, by conducting real time PCR after PIAS3 expression vector and the control expression vector are transfected into CD4+ cells separated from mouse.
Figure 7:
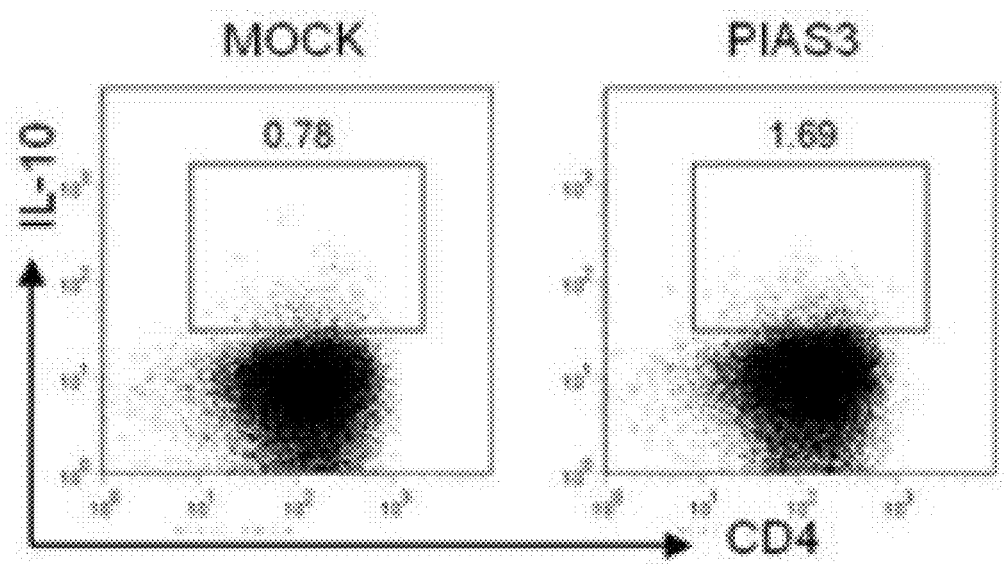
FIG. 7 illustrates the result of analyzing amount of cells expressing IL-10 by flow cytometry regarding the cells transfected with the PIAS3 expression vector and the control expression vector using the antibodies labeled with fluorescence for IL-10 and CD4.

As a result, it was clear that mRNA expression of IL-17 was suppressed in a state that the PIAS3, the inhibitor of STAT3, was overexpressed, and that the amount of IL-17 secretion was significantly reduced compared to the control according to the inhibited expression of IL-17 mRNA (see FIG. 6). Further, the IL-10 (representative cytokine expressed in Treg) expressing cell as measured by the flow cytometry was increased compared to the control when PIAS3 was overexpressed (see FIG. 7).

EXAMPLE 6

Analysis of Treatment Efficacy with Arthritis Animal Model Treated with PIAS3

To investigate if it is possible to actually treat immune diseases with the treatment of PIAS3, the STAT3 inhibitor, the arthritis-induced mouse were treated with PIAS3, and the enhancement of arthritis symptoms was observed through the following experiment. First, for arthritis animal model, type II collagen was intra-dermal injected to DBA1/J mouse. After arthritis was induced, the PIAS3 expression vector was injected into mouse by hydrodynamic injection which is a way of injecting using physical force through cell membrane into cytoplasm. Accordingly, the PIAS3 expression vector, diluted in normal saline solution was injected to tail vein, and for control, the mouse were injected with the mock vector. Further, since the arthritis was induced, arthritis index, tissue damage and inflammation level of the respective mouse groups were evaluated. Joints were taken from the respective mouse and the cartilage damage level was analyzed by immunohistochemical staining. Accordingly, joints of the respective mouse were taken, fixed in 10% neutral buffer formalin and demineralized with EDTA. After embedding in paraffin, the joint tissues were sliced into 7 um thick fragments and attached to the slides. After deparaffinization using xylene, hydration was performed with ethanol (high concentration (100%)->low concentration (10%)). Hematoxilin and eosin were used for the staining, and the articular tissues of the respective mouse were stained by Safranin O and Toluidine blue to detect proteoglycans included in the cartilage with optical microscope.

Figure 8:
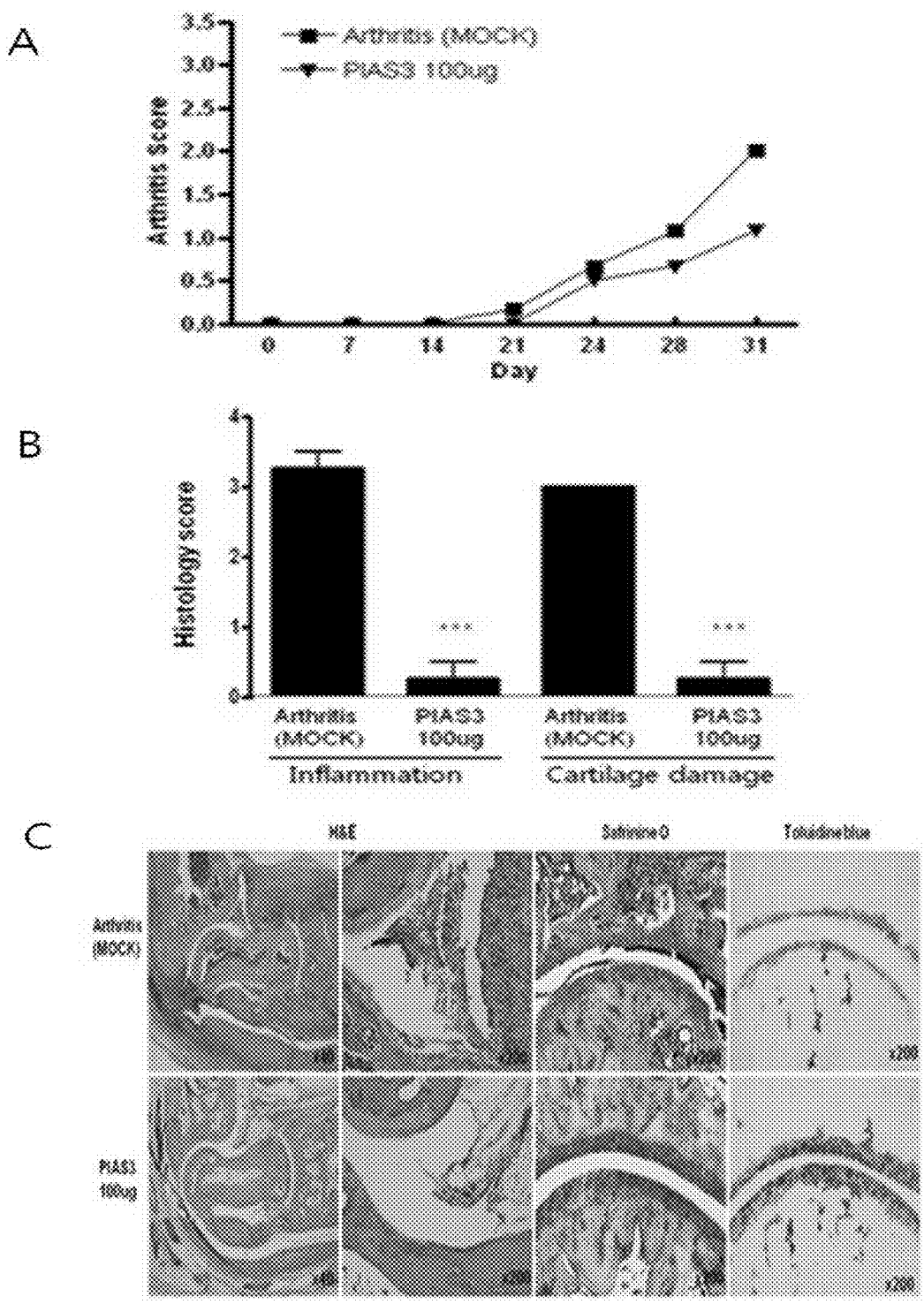
FIG. 8a is a graph scoring arthritis symptoms over time after the arthritis-induced mouse receive injection of PIAS3 expression vector and the control expression vector, in which the arthritis is induced with type II collagen.
FIG. 8b is a graph indexing and comparing the degree of inflammation and cartilage damage of the respective mouse.
FIG. 8c is an image showing degree of infiltration of the inflammatory cells in the articular tissues with immunohistochemical staining on the articular tissues of the respective mouse.

As a result, the arthritis-induced mouse injected with PIAS3 showed suppressed onset of arthritis over time, compared to the control injected with the mock vector (see FIG. 8a), and also showed greatly reduced inflammatory reaction and cartilage damage compared to the control (see FIG. 8b). Further, as a result of immunohistochemical staining, referring to FIG. 8c, the articular tissue damage was lessened in the PIAS3-injected mouse group compared to the control, in which the arthritis group (mock vector injected) showed inflammatory cells largely infiltrated, whereas the PIAS3-injected group showed noticeably-reduced inflammatory cells and particularly, suppressed damage of the cartilage tissues.

Accordingly, based on the above findings, the inventors were able to confirm the fact that PIAS3 according to the present invention can actually treat immune disease.

EXAMPLE 7

Analysis of Inflammatory Antibody Production Inhibitory Effect in PIAS3-Treated Arthritis Animal Model At Day 31 after inducing arthritis, blood samples were taken from the arthritis-induce mouse injected with PIAS3 expression vector at Example 6 and the control mouse group injected with mock vector, respectively. Serum was isolated from the blood samples, and IgG2a expression of the isolated serum was analyzed with ELISA. That is, the blood samples from the respective mouse groups were centrifuged, and IgG2a ELISA Quantitation set (Bethyl Laboratories) was used to analyze the IgG2a expression level of the isolated serum. To this end, purified mouse IgG2a coating antibody was diluted 1/100 in coating solution in 96 well plate, reacted overnight at 4° C., and non-specific binding was blocked after reaction with blocking solution. Further, mouse reference serum was diluted ½ each as standard sample, and the isolated serum and the ½ successively diluted mouse reference serum were added to the 96 well plate and reacted at room temperature. After 1 h, mouse IgG2a detection antibody attached with HRP was added, reacted at room temperature for 1 h, and TMB solution was added to present color, and the absorbance was measured at 450 nm wavelength.

As a result, referring to FIG. 9, the arthritis animal model injected with PIAS3 showed noticeably-suppressed IgG2a expression in serum, compared to the control. From the above finding, the inventors were able to confirm that PIAS3 can also actually suppress the production of IgG2a, the inflammatory antibody, in the arthritis mouse model.

EXAMPLE 8

Analysis of Inhibitory Effect on Inflammatory Cytokine, Angiogenesis Factor and Articular Damage Factor in PIAS3-Treated Arthritis Animal Model From the findings discussed above in each example, the inventors were able to confirm the fact that the PIAS3 according to the present invention inhibits expression of IL-17, the representative arthritis inflammatory cytokine, in the arthritis animal model in vivo, and suppresses articular damage and infiltration of the inflammatory cells. Accordingly, to investigate if PIAS3 also influences on the expression of the inflammatory cells within articular tissues, the inventors stained and observed the articular tissues. That is, joints of the respective mouse were taken from the arthritis-induced mouse injected with PIAS3 and the mouse injected with the mock vector of Example 6, and immunohistochemical staining of Example 6 was conducted. For staining, antibodies specific to IL-1b, IL-6, IL-17, TNF-a and RANK and VEGF (purchased from Sigma) were used to stain the respective factors.

As a result, the arthritis-induced control mouse group showed strong expression of inflammatory cytokines, L-1b, IL-6, IL-17 and TNF-a in cells, and particularly, showed strong infiltration of RNAK, the articular damage factor, and VEGF involved with angiogenesis. On the contrary, the arthritis mouse group treated with PIAS3 showed noticeably-suppressed expression of the inflammatory cytokines, articular damage factors and VEGF, compared to the control (see FIG. 10).

In consideration of the above findings, the inventors were able to confirm that PIAS3 can effectively suppress infiltration and proliferation of the inflammatory cells in the joints of the arthritis animal model.

EXAMPLE 9

Analysis of IL-17 Cytokind Inhibitory Effect in PIAS3-Treated Behcet's Disease

For Behcet's disease-induced mouse, mouse received herpes simplex virus (HSV) injection to develop Behcet's disease. The PIAS3 expression vector prepared at above-explained example of the present invention was injected into the mouse. Spleen and lymph node cells were separated from the mouse, and cells expressing IL-17 were analyzed by flow cytometry. For the flow cytometry, the cells were respectively treated with PerCP-labeled-mouse CD4 antibody and PE-labeled-mouse IL-17 antibody, and cells, which are CD4 T and which express IL-17, were analyzed. For control, the Bechet's disease-induced mouse were injected with the mock vector instead of the PIAS3 expression vector.

Figure 11:
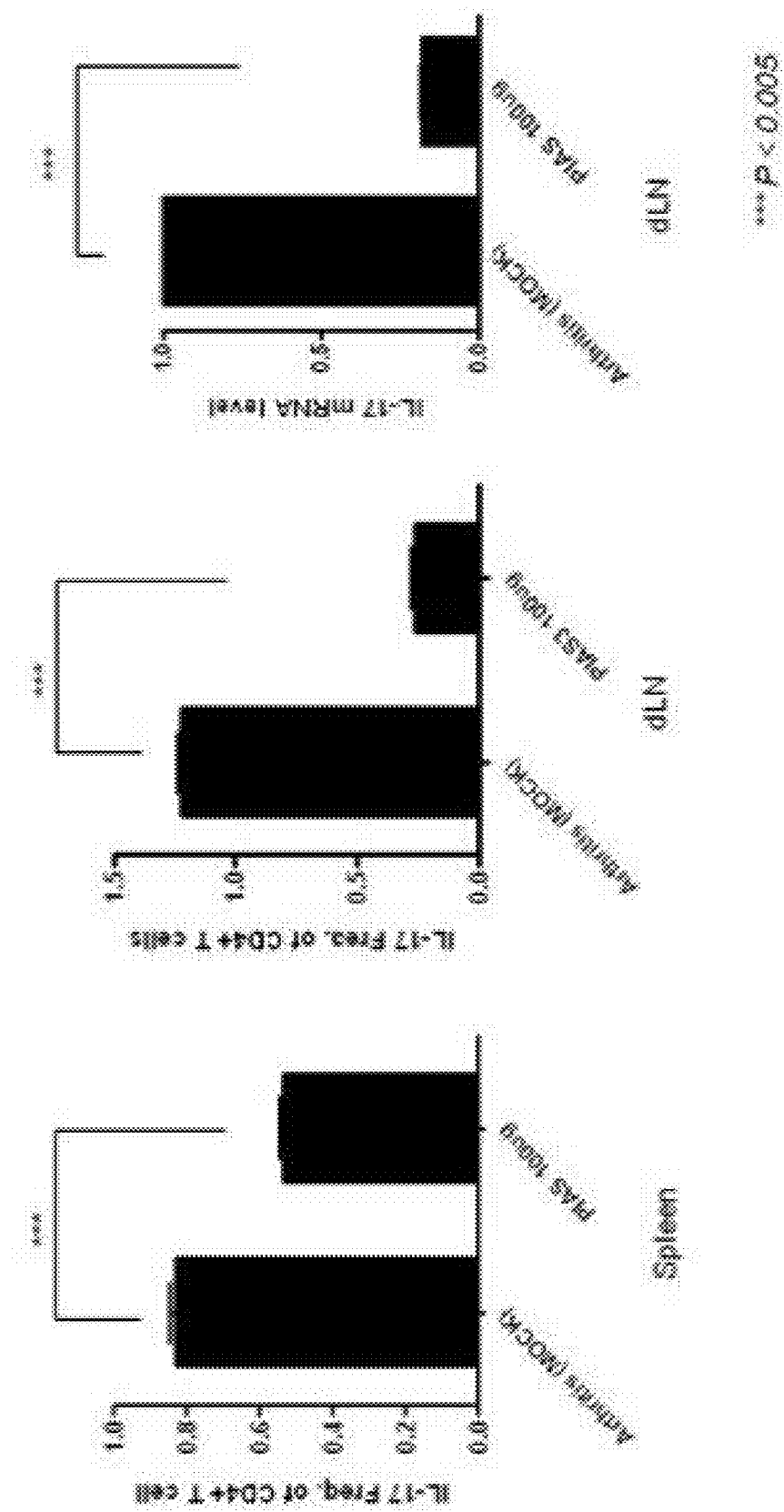
FIG. 11 illustrates the result of confirming amount of IL-17 expressed in cells by flow cytometry and PCR on the spleen and lymph node cells of the mouse infected with HSV and induced with Behcet's disease and receive injection of PIAS3 expression vector and control expression vector.

As a result, referring to FIG. 11, the Behcet's disease-induced mouse showed suppressed IL-17 expression by the PIAS3 treatment, and PIAS3 also decreased cells that express IL-17. This phenomenon of inhibiting IL-17 expression by PIAS3 was equally observed in the lymph node cells as well as spleen cells.

Further, the inventors separated cells from lymph nodes and extracted RNA from the cells to investigate the amount of expressed IL-17 at mRNA level, in which the amount of mRNA was analyzed by measuring amount of amplified DNA after PCR using primer to amplify IL-17 (see Example 5).

As a result, the amount of IL-17 expressed in lymph node cells of the PIAS3-injected Behcet's disease mouse group was noticeably-reduced compared to the control (injected with mock vector), and from this finding, it was confirmed that PIAS3 can actually decrease IL-17 in the Behcet's disease-induced living organism (see FIG. 11).

EXAMPLE 10

Analysis of Foxp3/Treg Increase and IL-17/Th17 Inhibitory Effect in Behcet's Disease Animal Model Treated with PIAS3

The inventors further investigated if the immune disease treatment effect of PIAS3 occurs via the mechanism of increasing Foxp3/Treg and inhibiting IL-17/Th17. Accordingly, the cells expressing Foxp3 and IL-17 of the spleen tissues of the mouse of Example 9 (i.e., spleen tissues of Behcet's disease-induced and then PIAS3-injected mouse & spleen tissues of mouse injected with mock vector) were examined under cofocallaser microscope. That is, after embedding the mouse spleen tissues with OCT compound, and then after rapid freezing with liquid nitrogen, the sample was sliced with sliding microtome to 7 um thickness and attached to the slides. After that, the fractions were immobilized in acetone, and non-specific response was blocked in 10% normal goat serum for 30 m. As for the first antibodies, FITC-labeled anti-Foxp3 Ab, PE-labeled anti-IL-17 Ab, APC-labeled anti-CD4 Ab, Allophycocyanin-labeled anti-CD25 Ab (Biolegend), biotinylated anti-CD4 Ab (BD Biosciences, San Jose, Calif.) were diluted in PBS (pH7.5), 1:100, and reacted at 4° C., overnight. On the next day, after washing with PBS and then reaction with streptavidin cy-3 at room temperature for 2 h, the stained tissues were analyzed under cofocallaser microscope.

As a result, IL-17 positive cells were meaningfully deceased in the PIAS3-treated group in a statistical way, and Foxp3 and Treg positive cells were noticeably increased in the PIAS3-treated group compared to the control (see FIGS. 12a and 12b).

Accordingly, from the above findings, the inventors were able to confirm that PIAS3 can ultimately prevent or treat immune diseases as well as arthritis, because PIAS3 inhibits expression of the inflammatory cytokine (IL-17) in the Behcet's disease-induced mouse in vivo, while at the same time increasing expression of Treg and Foxp3.

While the present invention has been particularly shown and described with reference to exemplary embodiments thereof, it will be understood by those skilled in the art that various changes in form and details may be made therein without departing from the spirit and scope of the invention as defined by the appended claims.

What is claimed is:

1. A method of treating Behcet's disease or arthritis comprising administering to a subject in need thereof a pharmaceutical composition comprising an expression vector comprising a nucleic acid encoding PIAS3 (protein inhibitor of activated STAT3) as an active ingredient.

2. The method of claim 1, wherein said nucleic acid consists of a sequence represented by SEQ ID NO:1.

3. The method of claim 1, wherein said nucleic acid decreases or suppresses differentiation of non-differentiated T cells into Th17 cells.

4. The method of claim 1, wherein said nucleic acid promotes or increases activity or expansion of regulatory T cells (Treg).

* * * * *

SEQUENCE LISTING

```
<160> NUMBER OF SEQ ID NOS: 9

<210> SEQ ID NO 1
<211> LENGTH: 2902
<212> TYPE: DNA
<213> ORGANISM: Homo sapiens
<220> FEATURE:
<223> OTHER INFORMATION: PIAS3 gene sequence

<400> SEQUENCE: 1
ggcatttgcg gccggcgcca gggtggagag ttgtgcgccg gtccctgggc ctgagctccg      60
gctccggctg gggcgcctgc gatgtctcaa gatggcggag ctgggcgaat taaagcacat     120
ggtgatgagt ttccgggtgt ctgagctcca ggtgcttctt ggctttgctg gccggaacaa     180
gagtggacgg aagcacgagc tcctggccaa ggctctgcac ctcctgaagt ccagctgtgc     240
ccctagtgtc cagatgaaga tcaaagagct ttaccgacga cgctttcccc ggaagaccct     300
ggggccctct gatctctccc ttctctcttt gcccctggc acctctcctg taggctcccc      360
tggtcctcta gctcccattc ccccaacgct gttggcccct ggcaccctgc tgggcccaa      420 gcgtgaggtg acatgcacc cccctctgcc ccagcctgtg caccctgatg tcaccatgaa      480
accattgccc ttctatgaag tctatgggga gctcatccgg cccaccaccc ttgcatccac     540
ttctagccag cggtttgagg aagcgcactt tacctttgcc ctcacacccc agcaagtgca     600
gcagattctt acatccagag aggttctgcc aggagccaaa tgtgattata ccatacaggt     660
gcagctaagg ttctgtctct gtgagaccag ctgcccccag gaagattatt ttcccccaa      720 cctctttgtc aaggtcaatg ggaaactgtg cccctgccg ggttaccttc ccccaaccaa      780
gaatggggcc gagcccaaga ggcccagccg ccccatcaac atcacacccc tggctcgact     840
ctcagccact gttcccaaca ccattgtggt caattggtca tctgagttcg gacggaatta     900
ctccttgtct gtgtacctgg tgaggcagtt gactgcagga acccttctac aaaaactcag     960
agcaaagggt atccggaacc cagaccactc gcgggcactg atcaaggaga aattgactgc    1020
tgaccctgac agtgaggtgg ccactacaag tctccgggtg tcactcatgt gcccgctagg    1080
gaagatgcgc ctgactgtcc cttgtcgtgc cctcacctgc gcccacctgc agagcttcga    1140
tgctgccctt tatctacaga tgaatgagaa gaagcctaca tggacatgtc ctgtgtgtga    1200
caagaaggct ccctatgaat ctcttatcat tgatggttta tttatggaga ttcttagttc    1260
ctgttcagat tgtgatgaga tccaattcat ggaagatgga tcctggtgcc caatgaaacc    1320
caagaaggag gcatctgagg tttgcccccc gccagggtat gggctggatg gcctccagta    1380
cagcccagtc caggggggag atccatcaga gaataagaag aaggtcgaag ttattgactt    1440
gacaatagaa agctcatcag atgaggagga tctgccccct accaagaagc actgttctgt    1500
cacctcagct gccatcccgg ccctacctgg aagcaaagga gtcctgacat ctggccacca    1560
gccatcctcg gtgctaagga gccctgctat gggcacgttg ggtggggatt tcctgtccag    1620
tctcccacta catgagtacc cacctgcctt cccactggga gccgacatcc aaggtttaga    1680
tttattttca tttcttcaga cagagagtca gcactatggc ccctctgtca tcacctcact    1740
agatgaacag gatgcccttg gccacttctt ccagtaccga gggacccctt ctcactttct    1800
```

```
gggcccactg gcccccacgc tggggagctc ccactgcagc gccactccgg cgcccctcc      1860 tggccgtgtc agcagcattg tggccctgg gggggccttg agggagggc atggaggacc       1920 cctgccctca ggtccctctt tgactggctg tcggtcagac atcatttccc tggactgagt     1980
tccctggatt atggaaactt cgctgtcccc caacactgag caagtatgct gtggagtccc     2040
aaccccagct actctgatcc ctctgggggc tctggccaag ggccagacag accttcacag     2100
atgcctactt ttggcctcat ctctgcctga caaggccagc acccaaaggg ttaatattta     2160
acctcttttt aaggacactg gggtctgttt ctggaaatgt tctttagatg gtggcacatt     2220
cctttgggta tgttaaccta ggcagtggga ggcaaatggg atggtatgtg agctaggaga     2280
agggctgaac cctcagcctt gactatgtct agagcctctt ggggaagggg cacctctctt     2340 gaacccaaa tgctctctct tcttattacc caaacccatg gctctatttc ttcttcacat      2400
ccattgtctc ttcatgtcta ttccattccc ttcggccaaa cagacaggtg gaaaaactga    2460
gacaggcagt tcagagatg gacagagaac tttattttgg attgtggatg tggacttttt     2520
tgtacataaa taagaaaaac caaaatactc caaagatgac ttcccctgcc tcctactcca    2580
gtatgacaga ggaggatgta aggccttagc catgatctgc aggggtctgg gagtcaggcc     2640
cggcctattg cttgggtctc tctctattta tatatctaag ttcacagtgt tcttattcc     2700 cccctaagct tctagaggct catggccctg tagttaggcc tggctcattc tgcacctttc    2760
cagggaggtg gaaggaccct gtgccctcct tcccaatctt cttttcagg ctcgccaagg     2820 cctaggacct atgttgtaat tttacttttt atttctaaag ttgtagtgaa gctctcaccc    2880
ataataaagg ttgtgaatgt tc                                              2902

<210> SEQ ID NO 2
<211> LENGTH: 21
<212> TYPE: DNA
<213> ORGANISM: Artificial Sequence
<220> FEATURE:
<223> OTHER INFORMATION: Foxp3 S

<400> SEQUENCE: 2
atgcctcctc ttcttccttg a                                                21

<210> SEQ ID NO 3
<211> LENGTH: 20
<212> TYPE: DNA
<213> ORGANISM: Artificial Sequence
<220> FEATURE:
<223> OTHER INFORMATION: Foxp3 AS

<400> SEQUENCE: 3
tgagaagggc agggcacaat                                                  20

<210> SEQ ID NO 4
<211> LENGTH: 20
<212> TYPE: DNA
<213> ORGANISM: Artificial Sequence
<220> FEATURE:
<223> OTHER INFORMATION: beta actin S

<400> SEQUENCE: 4
ggacttcgag caagagatgg                                                  20

<210> SEQ ID NO 5
<211> LENGTH: 22
<212> TYPE: DNA
```

```
<213> ORGANISM: Artificial Sequence
<220> FEATURE:
<223> OTHER INFORMATION: beta actin AS

<400> SEQUENCE: 5
tgtgttggcg tacaggtctt tg                                              22

<210> SEQ ID NO 6
<211> LENGTH: 20
<212> TYPE: DNA
<213> ORGANISM: Artificial Sequence
<220> FEATURE:
<223> OTHER INFORMATION: IL-17 sense primer

<400> SEQUENCE: 6
cctcaaagct cagcgtgtcc                                                 20

<210> SEQ ID NO 7
<211> LENGTH: 20
<212> TYPE: DNA
<213> ORGANISM: Artificial Sequence
<220> FEATURE:
<223> OTHER INFORMATION: IL-17 antisense primer

<400> SEQUENCE: 7
gagctcactt ttgcgccaag                                                 20

<210> SEQ ID NO 8
<211> LENGTH: 22
<212> TYPE: DNA
<213> ORGANISM: Artificial Sequence
<220> FEATURE:
<223> OTHER INFORMATION: beta-actin sense primer

<400> SEQUENCE: 8
gaaatcgtgc gtgacatcaa ag                                              22

<210> SEQ ID NO 9
<211> LENGTH: 22
<212> TYPE: DNA
<213> ORGANISM: Artificial Sequence
<220> FEATURE:
<223> OTHER INFORMATION: beta-actin antisense primer

<400> SEQUENCE: 9
tgtagtttca tggatgccac ag                                              22
```